United States Patent
Eacho et al.

(10) Patent No.: US 6,448,422 B1
(45) Date of Patent: Sep. 10, 2002

(54) CHROMOGENIC COMPOUND

(75) Inventors: Patrick Irving Eacho; Patricia Sue Foxworthy-Mason; Richard Waltz Harper; Ho-Shen Lin, all of Indianapolis; Jose Eduardo Lopez, Fishers; Michael Enrico Richett, Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 170 days.

(21) Appl. No.: 09/609,871

(22) Filed: Jul. 3, 2000

(51) Int. Cl.$^7$ .................................................. C07F 9/02
(52) U.S. Cl. ..................... 554/79; 554/78; 558/207; 558/208; 558/218
(58) Field of Search .............................. 554/78, 82, 79; 558/70, 207, 208, 218

(56) References Cited

U.S. PATENT DOCUMENTS

| | | |
|---|---|---|
| 4,810,636 A | 3/1989 | Corey |
| 4,932,871 A | 6/1990 | Bell et al. |
| 5,981,171 A | 11/1999 | Kuhns |
| 5,998,593 A | 12/1999 | Huff et al. |

OTHER PUBLICATIONS

WO patent 9615234, see citation and abstract, Caplus, AN 1996:417864, 1996.*

"IUPAC–IUB Combined Commission on Biochemical Nomenclature, Abbreviations and Symbols for Chemical Names of Special Interest in Biological Chemistry, Revised Tentative Rules (1965),"*Biochemistry,* vol. 5, No. 5, pp. 1445–1453 (1966).

Reynolds, et al., "1–Hexadecyl–2–Arachidonoylthio–2–deoxy–sn–Glycero–3–Phosphorylcholine as a Substrate for the Microtiterplate Assay of Human Cytosolic Phospholipase $A_2^1$," *Analytical Biochemistry* 217, pp. 25–31 (1994).

"Nomenclature of Phosphorus–Containing Compounds of Biochemical Importance," *Eur. J. Biochem.*, 79, pp. 1–9 (1977).

Arrigo, et al., "Preparative transformation of natural phospholipids catalysed by phospholipase D from Streptomyces," *Perkin 1*.

Hendrickson, et al., "Chiral synthesis of a dithiolester analog of phosphatidylcholine as a substrate for the assay of phospholipase $A_2$," *Journal of Lipid Research,* vol. 24, pp. 1532–1533 (1983).

Kucera, et al., "Hydrolysis of Thioester Analogs by Rat Liver Phospholipase $A_1$," *The Journal of Biological Chemistry,* vol. 263, No. 26, pp. 12964–12969 (1988).

Reynolds, et al., "Assay Strategies and Methods for Pospholipases," *Methods of Enzymology,* vol. 197, pp. 3–23 (1991).

Sutton, et al., "Cholesterol Esterase Catalyzed Hydrolysis of Mixed Micellar Thiophosphatidylcholines: A Possible Charge–Relay Mechanism," *Biochemistry,* vol. 30, pp. 5888–5893 (1991).

Twu, et al., "Hepatic Lipase Purification and Characterization," *Biochimica et Biophysica Acta.*, vol. 792, pp. 330–337 (1984).

Brockerhoff, et al., "Lipolytic Enzymes," *VI. Phospholipases: Carboxyl Esterases,* pp. 196–197.

(List continued on next page.)

*Primary Examiner*—Deborah D. Carr
(74) *Attorney, Agent, or Firm*—Francis O. Ginah; Arvie J. Anderson (57) ABSTRACT

This application relates to a novel compound of formula I, as defined herein, processes and intermediates for its preparation and the use of the compound of formula I as a substrate for a pharmaceutical screen.

5 Claims, 1 Drawing Sheet

OTHER PUBLICATIONS

Deckelbaum, et al., "Triacylglycerol and Phospholipid Hydrolysis in Human Plasma Lipoproteins: Role of Lipoprotein and Hepatic Lipase," *Biochemistry,* vol. 31, pp. 8544–8551 (1992).

Cohen, et al., "Hepatic lipase: new insights from genetic and metabolic studies," *Current Opinion in Lipidology,* vol. 10, pp. 259–267 (1999).

Cox, et al. "Preparation of thioester substrates and development of contiuous spectrophotometric assays forphospholipase A1 and monoacylglycerol lipase," *Journal of Lipid Research,* vol. 22, pp. 496–505 (1981).

Hendrickson, et al., "A facile asymmetric synthesis of glycerol phospholipids via tritylglycidol prepared by the asymmetric epoxidation of allyl alcohol. Thioester and thioether annalogs of phosphatidylcholine," *Chemistry and Physics of Lipids,* vol. 53, pp. 115–120 (1990).

"IUPAC–IUB Commission on Biochemical Nomenclature. The Nomenclature of Lipids: Notice of Revisions," *J. Biol. Chem.,* vol. 245, p. 1511 (1970).

Yu, et al. "Thio–Based Phospholipase Assay," *Methods in Enzymology,* vol. 197, pp. 65–74 (1991).

\* cited by examiner

Fig. 1

CHROMOGENIC COMPOUND

This invention is directed to a chromogenic compound, a thiophospholipid enzyme substrate, specifically thiophosphatidyl ethyleneglycol (thioPEG), which is useful as an indicator compound in an analytical test system. In particular, the present invention relates to a novel chromogenic substrate compound, its preparation and use in an assay and for the spectrophotometric detection of enzymes in a liquid test sample.

All biological membranes have the same classes of chemical compounds and a number of properties in common. These membranes are very dynamic structures with a movement that permits the cell as well as subcellular structures to adjust their shape and to move. The chemical components of membranes, which include lipids and protein, are well suited for the dynamic movement of membranes. Further, these membranes control the composition of the space they enclose by their ability to exclude a variety of molecules and via selective transport systems which permit the movement of molecules from one side to another. By controlling the translocation of substrates, cofactors and ions from one compartment to another, membranes modulate the concentration of substances, thereby exerting a strong influence on the body's metabolic pathways.

Lipids are a major component of membranes. The three major lipid components of cell membranes are phosphoglycerides, sphingolipids, and cholesterol. The phosphoglycerides and sphingomyelin, a sphingolipid containing phosphate, are classified as phospholipids.

Phospholipids, which are waxy solids, are found almost exclusively in cellular membranes and in the lipoproteins of blood plasma. Phospholipids thus serve primarily as structural elements and are never stored in large amounts. As their name implies, this group of lipids contains phosphorus in the form of phosphoric acid. The major phospholipids found in cells contain two fatty acid molecules which are esterified to the first and second hydroxyl groups of glycerol. The third hydroxyl group, at carbon atom 3, is esterified with phosphoric acid. Phospholipids contain a second alcohol which is also esterified to the phosphoric acid to form a phosphodiester; the second alcohol group is thus located on the polar head of the phospholipid molecule. The general structural formula of the phospholipids is shown below. RO—denotes the second alcohol group.

R = alkyl, alkenyl or alkynyl group

Different types of phospholipids are named according to the second alcohol at their polar heads. The most abundant phospholipids are the closely related phosphatidylethanolamine (also called cephalin) and phosphatidylcholine (also called lecithin), which contain ethanolamine and choline, respectively, at their heads. Each of these can occur in different forms depending on the fatty acids they contain.

Phospholipids readily undergo hydrolysis, catalyzed by acids, bases, or enzymes. Dilute base removes the two fatty acid groups of phosphatidylcholine, leaving the rest of the molecule intact. Strong base causes cleavage of both the fatty acids as well as the choline, leaving glycerol 3-phosphate, which can then be cleaved to yield glycerol and phosphoric acid by boiling with hydrochloric acid.

Different types of phospholipases are categorized based on the specific linkage for which they catalyze hydrolysis in the phospholipid molecule. Sites of action of phospholipases $A_1$, $A_2$, C and D on phosphatidylcholine are shown below.

$R_1$, $R_2$ = alkyl, alkenyl or alkynyl group

Via assay, phospholipase enzymatic activity may be measured.

The determination of phospholipase enzymes via assay is important in a variety of fields such as biochemical research, environmental and industrial testing, and medical diagnostics. The quantitation of enzyme levels in body fluids such as serum and plasma provides very useful information to the physician in diagnosing disease states and their treatment. In addition to being analytes of interest in biological fluids, enzymes can also serve as detection reagents in a variety of analytical systems such as immunoassays and nucleic acid hybridization techniques. In such systems, enzymes are useful directly or indirectly as indicators to monitor the extent of antigen-antibody binding or nucleic acid hybridization that occurs.

Accordingly, the desire to detect enzyme analyte and to use enzyme labels as a diagnostic tool in various analytical test systems has given rise to the development of optical indicator compounds for use in the detection and measurement of the activity of such enzymes. Typically, such known optical indicator compounds comprise a detectable chemical group, such as a fluorogen or a chromogen, which has been derivatized with an enzyme cleavable substrate group specific for the enzyme of interest. Such optical indicator. compounds exhibit an optical signal which is different from the optical signal which is provided by the cleaved native form of the fluorogen or chromogen. In principle, the enzyme cleaves the indicator compound to liberate the chromogen in the form of a distinctly fluorescent or colored product to provide a change in fluoroescence or color which is proportional to the amount of enzyme present which, in turn, can be correlated to the amount of analyte present in a liquid test sample.

Currently, there are numerous methods used to measure phospholipase enzymatic activity in an assay. Phospholipases are capable of cleaving thio ester bonds of an unnatural substrate. For example, phospholipase $A_2$ hydrolyzes and cleaves an sn-2 thio ester. The fact that hydrolysis releases a free thiol group has been utilized as the basis for a spectrophotometric assay shown below in Scheme A. See also, Lin Yu and Edward A. Dennis, *Methods in Enzymology*, Vol. 197, 65–75 (1991). Similarly, phospholipase $A_1$ hydrolyzes and cleaves an sn-1 thio ester. This sn-1 cleavage has also been utilized as the basis for a spectrophotometric assay. See, Kucera et al., *Journal of Biological Chemistry*, Vol. 263, 1264–1269 (1988). Further, the enzymatic activity of hepatic lipase, which catalzyes the hydrolysis of phospholipids, has also been measured via assay. See Deckelbaum R. J., et al., *Biochemistry*, 31, 8544–8551, 8545 (1992).

Scheme A

R = an alkyl, alkenyl or alkynyl group

Phospholipase $A_2$ cleaves the sn-2 oxy ester of phospholipids; it will also hydrolyze an sn-2 thio ester. As shown in Scheme B below, the liberated thiol is allowed to react with a thiol-sensitive reagent, and the formation is measured continuously by monitoring the increase in absorption associated with its production.

Scheme B

DTNB is used to detect the free thiol group. This reagent is commercially available from Aldrich (Milwaukee, Wis.). DTNB is preferable because it is sufficiently soluble in buffer such that stock solutions are aqueous.

The ability of phospholipases to cleave the thio ester bonds of unnatural substrates has also been utilized to develop continuous spectrophotometric assays for phospholipase $A_2$ (PLA2), phospholipase A1 (PLA1), phospholipase C (PLC), lysophospholipase and lipase. The detection methods available for phospholipase assays include titrametric, acidimetric, radiometric, nuclear magnetic resonance and others, including the thio assay.

The thio assay possesses many characteristics that recommend it as a general assay for phospholipases. The most important are that it is a continuous, spectrophotometric assay which is very convenient, it directly detects one of the products liberated upon hydrolysis, it is one of the more sensitive assays, and it is also suitable for detailed kinetic studies. The thio assay can be used for phospholipases $A_1$ and $A_2$ and with appropriate modification of the substrate would be applicable to other phospholipases. However, owing to the lack of commercial availability of thiophospholipid substrates and their complicated synthesis, the thio assay has not been used extensively.

Although commonly employed in phospholipase assays, natural phospholipid substrates bring disadvantages to an assay due to their long fatty acid chains. Phospholipids with long fatty acid chains solubilize into mixed micelles in the presence of detergents commonly used in an assay. Long-chain phospholipids also form vesicles and liposomes, which serve as a membrane model. Vesicle phospholipid packing and phase transition characteristics are a disadvantage since they both dramatically affect enzymatic activity. This presents a problem when comparing hydrolysis rates for different phospholipids. It is difficult to determine if an apparent preference of an enzyme for one phospholipid or another represents true specificity of the enzyme or is simply due to the different phospholipid packing of phase transition temperatures of the two substrates. These factors can also be a problem when performing assays containing surface active agents, such as inhibitors.

There are a number of synthetic phospholipid substrates available. A major issue to consider when selecting a phospholipase assay is the choice of an appropriate synthetic substrate from the large number of phospholipids available. A number of thiophospholipids have been synthesized as substrates, including stereospecific didecanoyl-thiophosphatidylcholine (thioPC) and its analog, didecanoyl-thio-phosphatidylethanolamine (thioPE). Using these substrates, the free thiol which is formed on hydrolysis of the thio ester bond is detected by the thio assay upon addition of either 5,5'-dithiobis(2-nitrobenzoic acid) (DTNB) or 4,4'-dithiobispyridine (DTP) as a thiol coloring reagent.

The thiol coloring reagents, DTP and DTNB, shown below, are routinely used to detect free thiol groups in the thio assay.

Both are commercially available. The choice of which thiol coloring reagent is more advantageous to use in the thio assay depends on pH, solubility, the effect on the extinction coefficient, and the effect on the enzyme. Another important consideration in choice of which thiol coloring reagent to use in an assay is whether or not either of the above thiol reagents affects the activity of an enzyme.

Thus, the thio assay is a method used to measure phospholipase activity in an assay. The thio assay is incompatible with free thiols or any other substance which would significantly reduce the diaryl disulfide bond in the thiol coloring reagent and, as a consequence, is generally limited to the measurement of pure phospholipases. However, the thio assay is convenient and reproducible when compared to other types of assays. In addition, the thio assay has a lower limit of detection of 1 nmol/min.

Recently, interest has grown in the study of assay strategies and methods for phospholipases including the thio assay. See for example Reynolds, et al., Assay Strategies and Methods for Phospholipases, *Methods in Enzymology*, Vol. 197, 3–23 (1991); See also, Lin Yu and Edward Dennis, Thio-Based Phospholipase Assay, *Methods in Enzymology*, Vol. 197, 65–75 (1991).

As mentioned above, thioPC and thioPE are effective substrates in the phospholipase assay. However, there are several limitations in the use of thioPC and thioPE as substrates. First, a lengthy synthesis is required for the preparation of these substrates. Secondly, thioPC requires additional portions of enzyme in order to obtain a detectable color. Further, thioPC hydrolyzes slowly and can thus cause low sensitivity within the assay. Finally, thioPE is increasingly unavailable due to its complicated synthesis method. Thus, there is a need for a better chromogenic substrate to replace thioPC and thioPE for use as a detection reagent in an assay.

The present invention, an unnatural substrate, is like thioPC substrates because it allows DTNB to be present throughout assay hydrolysis; and, thus, color is produced as the substrate is hydrolyzed. Therefore, only one incubation period is required compared to the two or more incubation periods required for thioPC, which further requires additional enzyme for color. Further, when the product of the reagent of the present invention reacts with a thio coloring agent, it does not cause an extraneous effect on the activity of the enzyme. Given the number of factors involved in choosing a thio coloring reagent for the thio assay, it is advantageous to minimize extraneous effect on the enzyme to the greatest extent possible. The invention is also an improvement over thioPE because its synthesis is much less complicated and should therefore be more generally available.

Thus the present invention relates to a novel chromogenic substrate which is a useful indicator compound in an analytical test system for the spectrophotometric detection of an enzyme in a liquid test sample. In particular, it relates to a better chromogenic substrate in the previously discussed phospholipase $A_1$ assay which is useful for spectrophotometric identification of potent inhibitors for treatment of phospholipase $A_1$ disorder. Thus, this invention relates to a new chromogenic substrate in the phospholipase assay, the process of preparing the substrate and the use of the substrate in a phospholipase assay to identify a potent inhibitor for a phospholipase related disorder.

Further, it is the object of the present invention to provide an assay which can be incorporated into the solid, porous matrix of an analytical test device as an indicator compound for the measurement of an enzyme incorporated therein or in a liquid test sample applied thereto.

Thus, in one aspect, the present invention is directed to a compound of formula I:

wherein:

each of Q and M is independently $C_5$–$C_{19}$ alkyl, alkenyl or alkynyl;

Y is $(CH_2)_2OH$ or $CH_2CH(OH)CH_2OH$;

or a non-interfering salt thereof.

The present invention is also directed to a compound of formula (I) in which each of Q and M is independently $C_5$–$C_{19}$ n-alkyl, n-alkenyl or n-alkynyl.

With reference to formula (I) above, the following are particular values:

each of M and Q is independently pentyl, hexyl, heptyl, nonyl, or tridecanyl; and Y is $(CH_2)_2OH$.

A more particular compound of formula (I) is one in which:

Q is nonyl.

Another particular compound of formula (I) is one in which:

each of Q and M is nonyl; and

Y is $(CH_2)_2OH$. (This particular compound is ThioPEG, or a salt thereof, as exemplified in Example 1)

As used above, and throughout the description of the invention, the following terms, unless otherwise indicated, shall be understood to have the following meanings:

"Alkenyl" means an aliphatic hydrocarbon group containing carbon-carbon double bonds.

"Alkyl" means an aliphatic hydrocarbon group which is straight or branched.

"Alkynyl" means an aliphatic hydrocarbon group containing carbon-carbon triple bonds.

"A compound of the present invention" or an equivalent expression, is meant to embrace a compound of general formula (I) as hereinbefore described, which expression includes a salt, where the context so permits. Similarly, reference to an intermediate, whether or not it itself is claimed, is meant to embrace a salt, where the context so permits. For the sake of clarity, particular instances when the context so permits are sometimes indicated in the text, but these instances are purely illustrative and it is not intended to exclude other instances when the context so permits.

This invention provides, in addition, a process for preparing a compound of formula I (or a non-interfering salt thereof) comprising:

(i) for a compound of formula I in which Y is $(CH_2)_2OH$, phosphorylating the hydroxy group of a corresponding compound of formula II:

II using 2-chloro phospholane-2-oxide followed by treatment with water; or (ii) phosphorylating the hydroxy group of an alcohol of forumula Y-OH using a compound of formula III:

III followed by hydrolysis;

whereafter when a non-interfering salt is required such salt may be made with a base which affords a non-interfering cation;

wherein, unless otherwise specified, each of Q, Y and M has values as defined above.

Another particular compound is the compound of formula I which is (1-decanoylthio-1-deoxy-2-decanoyl-sn-glycero-3-phosphoryl)ethylene glycol.

Another particular compound is the compound of formula I which is 1-decanoylthio-1-deoxy-2-decanoyl-sn-glycero-3-phosphoryl-1'-sn-glycerol.

An additional aspect of the present invention is directed to a compound of formula III:

III wherein each of the values of Q and M is as defined above.

In the reactions described herein it may be necessary to protect reactive functional groups, for example hydroxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, Inc., 1999.

Thus, there is provided a process for preparing a novel compound of formula I as provided in any of the above descriptions which is selected from any of those described in the examples. This includes phosphorylation of the deprotected hydroxy group of a compound of formula II using commonly known phosporylating agents. The preferred phosphorylating agent, when Y is $(CH_2)_2OH$, is 2-chlorophospholane-2-oxide. The preferred temperature for this reaction is from about 10° C. to about 50° C. The most preferred temperature for this reaction is about ambient temperature.

The present invention further provides a method of using the compound of formula I as an indicator in an analytical test system for the measurement of enzymatic activity in a liquid test sample.

The invention further provides for a method of using the compound of formula I as an indicator compound in analytical test systems for the measurement of enzymatic activity in a liquid test sample for the treatment of diseases.

The invention also provides for a method of using the compound of formula I in a phospholipase A1 or B assay to spectrophotometrically identify an inhibitor for the treatment of a phospholipase $A_1$ related disorder.

The invention further provides for a method of using the compound of formula I in the phospholipase $A_1$ assay to identify a hepatic lipase inhibitor.

Thus, the present invention relates to a novel chromogenic substrate for use in an assay to afford identification of enzymatic activity in a screen.

The present invention further relates to a chromogenic substrate which may be used in an assay and will allow identification of a potent inhibitor such as a hepatic lipase inhibitor.

The present invention also relates to a chromogenic substrate which may be used in a phospholipase $A_1$ assay and which will allow the identification of a potent inhibitor for the treatment of a phospholipase $A_1$ related disorder(s).

The present invention also relates to a chromogenic substrate which may be used in a phospholipase $A_1$ assay and which will allow the identification of a potent inhibitor for the treatment of a phospholipase $A_1$ related disorder such as a hepatic lipase inhibitor to be used as a cardiovascular protective agent for raising plasma high-density lipoprotein (HDL) levels. In particular, this compound is a chromogenic substrate in the hepatic lipase inhibition assay in the presence of DTNB (Ellman's Reagent), replacing thioPC.

Another special embodiment of the method of the present invention is the use of a compound of formula I in a phospholipase $A_1$ assay to spectrophotometrically identify an inhibitor for the treatment of a phospholipase $A_1$ related disorder.

Another special embodiment of the method of the present invention is the use of a substrate of formula I in a phospholipase $A_1$ assay to identify a hepatic lipase inhibitor.

It is a further object of the invention to provide a kit or test device which may be effectively utilized for carrying out the novel uses of the invention.

In another aspect, a kit or test device is provided and comprises a compound of forumula I in a suitable container. Depending upon the purpose of the kit, a kit according to the invention can further include an additional or additional containers that contain, for example, a control reagent, a coloring agent and other reagents suitable for running an assay of interest.

In another aspect, the kit or test device for measurement of enzymatic activity contains a carrier matrix incorporated with the compound of formula I.

Thus, a novel chromogenic substrate is provided which has valuable properties. The substrate may be particularly useful in an assay for identification of an inhibitor of an enzyme. The inhibitor, in turn, may be useful for treatment of a phospholipase $A_1$ related disorder. The substrate could be used in an assay to identify a hepatic lipase inhibitor, for example, which could then be used as cardiovascular protective agents for raising plasma high-density lipoprotein (HDL) levels.

In general, a compound of formula I may be prepared according to the route outlined in Scheme B below, and described in the Examples, in which each of M and Q, respectively, represents a value defined for the groups M and Q.

In Scheme C below, the hydroxy group of the epoxide of formula 1 is protected with a suitable protecting group such as trityl to form a protected epoxide of formula 2. The epoxide, formula 2, is ring opened with a thio fatty acid nucleophile to form the compound of formula 3. A compound of formula 3 is combined with sodium methoxide in methanol (methanolysis) yielding the compound of formula 4.

For a compound in which M is the same as Q, a compound of formula 5 is obtained via diacylation when compound 4 is treated with an activated derivative of an acid of formula QCOOH, for example, using the acid chloride in the presence of a base such as pyridine and a solvent such as methylene chloride, as described in Example 1. The compound of formula 5 is then deprotected to form a compound of formula II. The compound of formula II is phosphorylated as described in the Examples to form compound I.

Scheme C

Utilizing an alternative procedure, Scheme D, values of M and Q may be different. In the alternative procedure, the epoxide of formula 2 is ring opened with a thio fatty acid nucleophile of formula MCOS⁻ where M is as previously defined, to form compound 8. An example of a thio fatty acid nucleophile is thio decanoyl acid sodium salt. The compounds of formula 5, II, and I are formed using methods similar to those described above in Scheme B and in the Examples.

Alternatively, as shown in Scheme D below, compound II may be phosphorylated with $POCl_3$ to form a compound of formula III. The compound of formula III may be utilized to prepare the compounds of formula I wherein Y is $CH_2CH_2OH$ (compound 9) or $CH_2CH_2OHCH_2OH$ (compound 10). To prepare compound 9 from a compound of formula III, ethylene glycol is treated with the compound of formula III, followed by an acid hydrolysis wash. Compound 10 may similarly be formed via reaction of a compound of formula III with glycerol followed by acid hydrolysis wash.

Scheme D

If not commercially available, the necessary starting materials for the preparation of a compound of formula I may be prepared by procedures which are selected from standard techniques of organic chemistry, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

As mentioned above, the invention includes acceptable salts of the thioPEG substrate compounds defined by the above formula I. Acceptable salts are those that do not interfere with analytical methods and procedures. Such salt may be made with a base which affords an acceptable cation, which includes alkali metal salts (especially sodium and potassium), alkaline earth metal salts, aluminum salts and ammonium salts, as well as salts made from organic bases such as triethylamine, morpholine, piperidine and triethanolamine. The potassium and sodium salt forms are particularly preferred.

Selective methods of protection and deprotection are well known in the art for preparation of compounds such as those corresponding to a compound of formula I.

Figure 1:
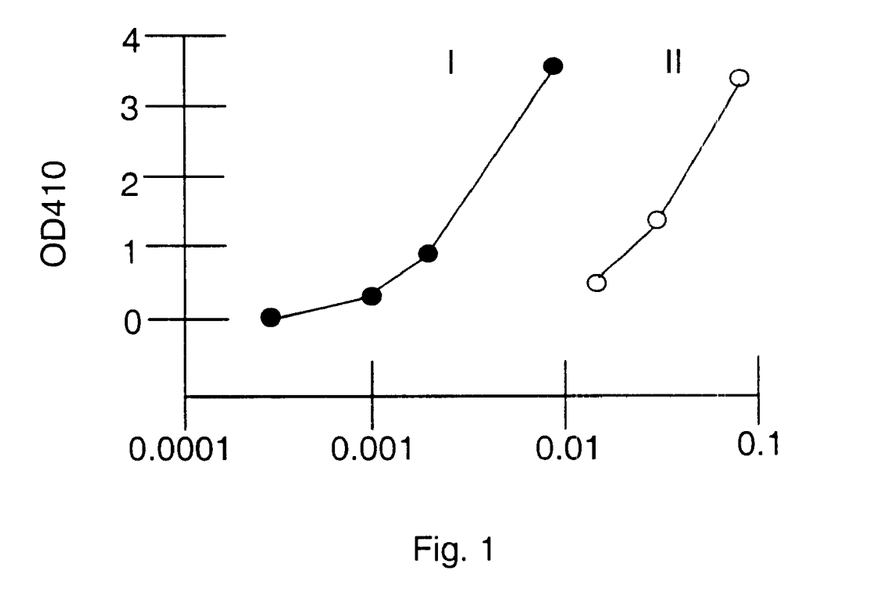
FIG. 1 shows the hydrolysis of thioPEG and thioPC substrates by Hepatic Lipase. Hepatic Lipase enzyme was diluted 1, 32 or 64 fold for thioPC and 100, 500, 1000 or 5000 fold for thioPEG. Hydrolysis was measured by the papain thiol detection system (discussed below). The Y-axis shows the Optical Density at 410 nM. The X-axis shows the Relative Enzyme Concentration. Data curve I represents 0.5 mM thioPEG and Data Curve II represents 1.0 mM thioPC.

The instant invention, thioPEG, is an improvement over substrates currently used in the phospholipase assay, such as thioPC. As the figure illustrates, thioPEG is hydrolyzed much faster than thioPC. Since the enzyme hydrolyzes thioPC much more slowly, there is much less product formed in the reaction and thus, less sensitivity for the assay. Due to increased enzymatic activity with thioPEG, therefore, sensitivity of the assay is increased.

The invention also has the additional advantage of requiring fewer incubation periods in order to obtain detectable color. For example as shown in Scheme D below, thioPC substrate requires a reaction coupled with an enzymatic detection process for the liberated thiol-lysophospholipid which has two additional incubation periods in the papain system. L-BAPNA is an abbreviation for N-benzoyl-L-arginine, p-nitroanilide, hydrochloride.

In Scheme E, below, thioPC is combined with hepatic lipase and incubated for about 30 minutes yielding a free-thiol lysophospholipid. The free-thiol lysophospholipid is combined with inactive papain-S—S—CH$_3$ and incubated for 60 minutes, yielding activated papain-SH enzyme. Activated papain-SH enzyme is combined with a coloring agent, L-BAPNA, and incubated for 60 minutes yielding a colored product, p-nitro aniline. ThioPEG substrate is an improvement since it requires only a single incubation period to yield detectable color.

Scheme E

ThioPEG is more direct because the assay has DTNB present throughout the hydrolysis so that color is produced as the substrate is hydrolyzed. As the procedural Scheme F shows below, there is only one incubation time for thioPEG.

Using ThioPEG as a substrate has an additional advantage because the DTNB system is a chemical reaction as opposed to an enzymatic reaction. Since the DTNB system is a chemical reaction, there is a decreased chance for an inhibitor, such as hepatic lipase, to interfere with the detection system itself.

Hepatic Lipase Phospholipase Assay

Reagents

Substrate Buffer A: 100 mM Hepes, pH 8.3 at 37° C.

Substrate Buffer B: 100 mM Hepes, pH 8.3 at 37° C with 6.83 mM Triton X100

ThioPEG: Molecular wt. of 540

Recombinant Hepatic Lipase

Thiophospholipid: about 0.42 mM thiophospholipid in chloroform

DTNB Solution: about 50 nM DTNB in DMSO (dimethyl sulfoxide)

Hepes Buffer A

For Hepes Buffer A, there is 2.4 g Hepes/100 mL water. Therefore 36 grams of Hepes is dissolved in 1500 mL of water. The mix solution's pH is adjusted to pH83 at 37° C. and brought up to 1500 mL with water. 500 mL of Buffer A is retained for the Protein Buffer.

Hepes Buffer B

To the remaining 1000 mL of Hepes Buffer A, 4.49 g of Triton X-100 is added and then the combination mixed on a stir plate. It is optimal that stock Buffer A not be too cold or Triton X-100 will take a long time to go into solution ThioPEG Substrate Solution For 0.42 mM substrate stock, use 0.227 mg of thioPEG/ mL of Substrate Buffer B. Approximately 20 mg of sn-1 thiol substituted Phosphatidyl Ethylene Glycol (see Examples for preparation method) is weighed into a vial, such as a scintillation vial. Enough chloroform should be added to make a 2.043 mg/mL solution. Sonicate the solution briefly until well dissolved. Next, pipette 1 mL of chloroform/substrate solution into each scintillation vial.

Scheme F

This should give enough substrate for one full 96 well plate. Each vial is dried with nitrogen until solvent removed, swirling each vial simultaneously such that a thin film of substrate will be easily reconstituted in each buffer. Each vial is then frozen.

Daily stock preparation is performed for 9 mL of substrate (one microtiter plate). On the day of the assay, the substrate vial is removed from the freezer and combined with 9 mL of pre-warmed (37° C.) substrate buffer (the final concentration is 0.227 mg/mL). Place the buffer in a 37° C. water bath. Sonicate for 5 minutes or vortex until solution is clear before use.

Enzyme Solution

The enzyme is stored at −80° C. in 100 or 50 μL portions. A 0.406 mg/mL recombinant hepatic lipase stock requires a 50 fold dilution. Therefore, to a 50 μl or 100 μl enzyme aliquot, 2450 μl or 4900 μl, respectively, of substrate Buffer A (protein buffer) should be added. The enzyme should then be stored on ice until ready to use. The protein concentration of enzyme is about 0.406 mg/mL.

DTNB Solution

To make a 20 mg/mL stock solution, 2–3 mg of DTNB is weighed and then mixed with an appropriate amount of 100% DMSO (dimethyl sulfoxide) to make the desired concentration. This mixture is sonicated for five minutes.

The above solution should be diluted 10 fold with substrate Buffer B (concentration now 2 mg/mL). Then to the thioPEG substrate solution, add 60 μl of dilute DTNB per mL of thioPEG substrate solution. Thus for 9 mL of substrate, 540 microliters of dilute DTNB (final concentration in substrate solution=0.11 mg/mL).

Table 1 below shows final assay volumes and concentrations of various components used following the above procedure.

TABLE 1

Final Assay Volumes and Concentrations
Hepatic Lipase Phospholipase Assay

| Component | Assay Volume | Final Concentration |
|---|---|---|
| HL | 10 μl | 12.5 nM |
| Test Cpd. | 10 μl | Varies |
| ThioPEG Substrate (stock = 0.42 mM + substrate buffer) | 80 μl | 90 mM Hepes 5.8 mM TX100 0.336 mM ThioPEG (0.06 mol fraction) 0.088 mM DTNB/mL |

Sample Preparation

The test compound is dissolved in pure DMSO at 1 μM (1000 nM). As shown below in Table 2, assay concentrations are 10, 1, 0.1, 0.33, 0.011, 0.0037, 0.0012 and 0.00041 μM. Table 2 shows the assay concentrations and the corresponding volume of stock and 10% DMSO for each concentration.

TABLE 2

Assay concentrations for compound preparation

| Concentration (μM) | Assay Conc (μM) | Microliters of stock solution | Dilutent |
|---|---|---|---|
| 100 | 10 | 50 of 1 mM in straight DMSO | 450 μl of WATER |
| 10 | 1 | 5 μl of 100 μM | 450 μl 10% DMSO |
| 1 | 0.1 | 50 μl of 10 μM | 450 μl 10% DMSO |
| 0.33 | 0.033 | 200 μl of 1 μM | 400 μl 10% DMSO |
| 0.11 | 0.011 | 200 μl of 0.33 μM | 400 μl 10% DMSO |

TABLE 2-continued

Assay concentrations for compound preparation

| Concentration (μM) | Assay Conc (μM) | Microliters of stock solution | Dilutent |
|---|---|---|---|
| 0.037 | 0.0037 | 200 μl of 0.11 μM | 400 μl of 10% DMSO |
| 0.012 | 0.0012 | 200 μl of 0.037 μM | 400 μl of 10% DMSO |
| 0.0041 | 0.00041 | 200 μl of 0.012 μM | 400 μl of 10% DMSO |

Assay Procedure

Using a spectrometer, DTNB is used as a thiol coloring reagent with an incubator temperature of 37° C. Substrate Buffer B is placed in a 37° C. water bath to pre-warm. The substrate is removed from the freezer and 9 mL of substrate Buffer B, 100 mM Hepes, 6.83 mM Tx-100) is added, sonicated for 5 min. and then kept in a 37° C. water bath. Dilutions of the test compound are next made in preparation for assay.

10 μl of the diluted test compound are transferred via pipette into the wells. Control wells receive 10 μl each of 10% DMSO and enzyme solution, while blank wells receive 10 microliters of 10% DMSO and 10 microliters of saline (no enzyme).

Next, DTNB is weighed and diluted to 20 mg/mL with DMSO. The DTNB is then diluted 10 fold with the substrate Buffer B. 540 μl of diluted DTNB is added to 9 ml of ThioPEG and mixed well.

The stock enzyme is diluted with Buffer A. Next, 10 microliters of protein solution is added to each well except the blank, and the wells mixed. The stock solution and test compounds are incubated at 37° C. for 10 min. At 10 minutes, 80 microliters of substrate are added to each well. The plate is then placed in the spectrometer and read at 412 nM every 2 minutes for 30 minutes.

The compound of the present invention and its methods of preparation will appear more clearly from the examination of the following examples which are presented as an illustration only and are not to be considered as limiting the invention in its scope.

The following Examples are provided to further describe the invention and are not to be construed as limitations thereof.

The abbreviations, symbols and terms used in the examples have the following meanings.

Ac=acetyl

Anal.=elemental analysis calcd=calculated

Cpd.=compound

DMF=dimethylformamide

DMSO=dimethylsulfoxide

Et=ethyl

EtOAc=ethyl acetate

EtOH=ethanol

EtSH=ethanethiol

ESIMS=Electrospray Ionization Mass Spectrometry

FAB=Fast Atom Bombardment (Mass Spectrascopy)

FDMS=field desorption mass spectrum

Hex=hexanes

HL=Hepatic Lipase

HPLC=High Performance Liquid Chromatograph

HRMS=high resolution mass spectrum

IR=Infrared Spectrum

Me=methyl
MeI=methyl iodide
MeOH=methanol
MPLC=Medium Pressure Liquid Chromatography
NMR=Nuclear Magnetic Resonance
PPA=polyphosphoric acid
Rochelle's Salt=potassium sodium tartrate
RPHPLC=Reversed Phase High Performance Liquid Chromatography
SiO$_2$=silica gel
SM=starting material
Temp.=temperature
TFA=trifluoroacetic acid
THF=tetrahydrofuran
TLC=thin layer chromatography

EXAMPLE 1

Preparation of (1-Decanoylthio-1-deoxy-2-decanoyl-sn-glycero-3-phosphoryl) ethylene glycol

A. (S)-(−)-Glycidyl Triphenylmethyl Ether

A solution of trityl chloride (48.25 g, 173 mmol) in anhydrous CH$_2$Cl$_2$ (150 mL) was added to a stirred solution of (S)-(−)-glycidol (12.21 g, 164 mmol) and triethylamine (34.5 mL, 247 mmol) in anhydrous CH$_2$Cl$_2$ (250 mL) at −20° C. under a N$_2$ atmosphere. After 2 h, CH$_2$Cl$_2$ was removed under vacuum. The mixture was taken up in EtOAc (500 mL) before it was washed with H$_2$O (2×200 mL). The organic layer was dried, filtered and concentrated to give the crude title compound (67.9 g) contaminated with trityl alcohol, which can be removed by chromatography.

$^1$H-NMR (CDCl$_3$) δ7.46 (d, J=7.8 Hz, 6H), 7.21–7.33 (m, 9H), 3.33 (d, J=8.4 Hz, 1H), 3.14 (br s, 1H), 3.09–3.17 (m, 1H), 2.78 (t, J=4.2 Hz, 1H), 2.63 (m, 1H).

B. 1-Acetylthio-1-deoxy-3-(triphenylmethyl)-sn-glycerol

Thioacetic acid (8.75 mL, 122 mmol) and thioacetic acid potassium salt (13.98 g, 122 mmol) were sequentially added to a stirred solution of crude (S)-(−)-glycidyl triphenylmethyl ether (12.08 g, 38.2 mmol) in anhydrous DMF (130 mL) at 0° C. under a N$_2$ atmosphere. The resultant mixture was stirred at 0° C. for 0.5 h, then at ambient temperature for an additional 1.5 hr. The reaction mixture was taken up in toluene (1.3 L), washed with H$_2$O (2×650 mL), dried and filtered. After concentration in vacuo, the residue was chromatographed on silica (CH$_2$Cl$_2$) to give the title compound (6.01 g, 40% yield) as a yellow oil.

IR (CHCl$_3$) 3570, 1689 cm$^{-1}$;

$^1$H NMR (CDCl$_3$) δ2.32 (s, 3H), 2.52 (br s, 1H), 2.99–3.05 (m, 1H), 3.11–3.24 (m, 3H), 3.89 (br s, 1H), 7.22–7.36 (m, 9H), 7.41–7.45 (m, 6H);

FDMS m/e 392 (M$^+$); [α]$_D$+7.30 degrees (c 0.0205 g/mL, CHCl$_3$)

Elemental Analysis for C$_{24}$H$_{24}$O$_3$S.0.3H$_2$O:

| Calculated: | C, 72.44; H, 6.23; |
|---|---|
| Found: | C, 72.20; H, 6.08. |

C. 1-Thio-1-deoxy-3-(triphenylmethyl)-sn-glycerol

Anhydrous methanol (20 mL) was added to a stirred suspension of sodium (1.21 g, 52.8 mmol) in anhydrous THF (20 mL) at 0° C. under a nitrogen atmosphere. The resultant mixture was allowed to stir at ambient temperature until sodium was consumed. Then a solution of 1-acetylthio-1-deoxy-3-(triphenylmethyl)-sn-glycerol (5.94 g, 15.1 mmol) in anhydrous THF (40 mL) was added via cannula to the NaOMe solution, and the reaction mixture was stirred for 2 h. After dilution with EtOAc (600 mL), the mixture was sequentially washed with half-saturated aqueous NaCl solution (250 mL) containing acetic acid (3.46 mL, 60.4 mmol), then with saturated NaHCO$_3$ solution (100 mL). The organic layer was dried, filtered and concentrated in vacuo. The residue was chromatographed on silica to give the title compound (4.14 g, 78% yield) as a colorless oil. IR (CHCl$_3$) 3580, 1449 cm$^{-1}$;

$^1$H NMR (CDCl$_3$) δ1.31 (t, J=8.6 Hz, 1H), 2.51 (d, J=4.8 Hz, 1H), 2.64–2.77 (m, 2H), 3.19–3.29 (m, 2H), 3.80–3.85 (m, 1H), 7.23–7.36 (m, 9H), 7.42–7.46 (m, 6H);

ESIMS m/e 349 (M$^+$−1); [α]$_D$+3.26 degrees (c 0.0129 g/mL, CHCl$_3$).

Elemental Analysis for C$_{22}$H$_{22}$O$_2$S.0.2H$_2$O:

| Calculated: | C, 74.62; H, 6.38; |
|---|---|
| Found: | C, 74.43; H, 6.35. |

D. 1-Decanoylthio-1-deoxy-2-decanoyl-3-(triphenylmethyl)-sn-glycerol Anhydrous pyridine (3.66 mL, 45.2 mmol) and decanoyl chloride (6.08 mL, 29.4 mmol) were sequentially added to a stirred solution of 1-thio-1-deoxy-3-(triphenylmethyl)-sn-glycerol (3.96 g, 11.3 mmol) in anhydrous $CH_2Cl_2$ (40 mL) at 0° C. under a nitrogen atmosphere. The cold bath was removed and the mixture was stirred for 1 h. After dilution with EtOAc (250 mL), the mixture was washed with $H_2O$ (100 mL×2), dried, filtered and concentrated. The residue was chromatographed on silica (20% EtOAc in hexane) to give the title compound (7.01 g; 94% yield) as a colorless oil.

IR ($CHCl_3$) 1733, 1688 $cm^{-1}$;
$^1$H NMR ($CDCl_3$) δ0.88 (br t, J=6.3 Hz, 6H), 1.20–1.35 (m, 24H), 1.55–1.70 (m, 4H), 2.32 (t, J=7.4 Hz, 2H), 2.48 (t, J=7.5 Hz, 2H), 3.07–3.32 (m, 4H), 5.11–5.16 (m, 1H), 7.20–7.32 (m, 9H), 7.40–7.44 (m, 6H);
FDMS m/e 659 ($M^+$); $[\alpha]_D$+16.93 degrees (c 0.0087 g/mL, $CHCl_3$).

E. 1-Decanoylthio-1-deoxy-2-decanoyl-sn-glycerol

Triethylsilane (29.4 mL, 182 mmol) and trifluoroacetic acid (5.90 mL, 75.9 mmol) were sequentially added to a stirred solution of 1-decanoylthio-1-deoxy-2-decanoyl-3-(triphenylmethyl)-sn-glycerol (10.0 g, 15.2 mmol) in anhydrous 1,2-dichloroethane (100 mL) at −32° C. (ethylene glycol/methanol/dry ice) under a nitrogen atmosphere. The resultant yellow solution was allowed to warm to −25° C. where it was stirred for an additional 1.5 h. While stirring vigorously at −25° C., the mixture was slowly and sequentially treated with cold THF (100 mL) and cold saturated $NaHCO_3$ (150 mL) and cold hexane (200 mL). The mixture was allowed to warm to ambient temperature where to it were added water (200 mL) and hexane (200 mL). The organic layer was separated and the aqueous layer was extracted with hexane (200 mL). The combined organic layers were washed with brine (200 mL×2), dried over $Na_2SO_4$, filtered and concentrated in vacuo. The residue was chromatographed on silica (0–20% EtOAc in hexane) to give the title compound (4.69 g, yield 74%) as a colorless oil.

IR ($CHCl_3$) 3520, 1732, 1687 $cm^{-1}$;
$^1$H NMR ($CDCl_3$) δ0.88 (t, J=6.6 Hz, 6H), 1.20–1.35 (m, 24H), 1.60–1.70 (m, 4H), 2.20 (br s, 1H), 2.32 (t, J=7.5 Hz, 2H), 2.58 (t, J=7.5 Hz, 2H), 3.11 (dd, J=14.3, 5.4 Hz, 1H), 3.27 (dd, J=14.3, 6.3 Hz, 1H), 3.62–3.72 (m, 2H), 4.92–4.99 (m, 1H);
FDMS m/e 416 ($M^+$); $[\alpha]_D$+1.31 degrees (c 0.1002 g/mL, $CHCl_3$).

Elemental Analysis for $C_{23}H_{44}O_4S$:

| Calculated: | C, 66.30; H, 10.64; |
|---|---|
| Found: | C, 66.36; H, 10.70. |

F. (1-Decanoylthio-1-deoxy-2-decanoyl-sn-glycero-3-phosphoryl)oxy]ethylene glycol Anhydrous 4-methylmorpholine (1.83 mL, 16.5 mmol) and 2-chlorophospholane-2-oxide (1.51 mL, 16.5 mmol) were sequentially added to a stirred solution of 1-decanoylthio-1-deoxy-sn-glycerol (4.59 g, 11.0 mmol) in anhydrous toluene (300 mL) at ambient temperature. The resultant mixture was stirred for 45 min to form a suspension. After filtration and washing with toluene (30 mL), the filtrate was treated with THF (250 mL) and $H_2O$ (150 mL). Then the mixture was stirred vigorously overnight. After concentration in vacuo at 40° C., the residue was chromatographed on silica [gradient 0–15% (MeOH/$H_2O$; 19/1) in $CHCl_3$] to give the title compound (4.10 g, 69% yield) as a wax like compound.

IR ($CHCl_3$) 3660, 3388 (br), 1733, 1695 $cm^{-1}$;
$^1$H NMR ($CDCl_3$) δ0.88 (t, J=6.4 Hz, 6H), 1.20–1.38 (m, 24H), 1,55–1.68 (m, 4H), 2.15 (br s, 1H), 2.28 (t, J=7.5 Hz, 2H), 2.53 (t, J=7.5 Hz, 2H), 3.07 (dd, J =14.2, 8.0 Hz, 1H), 3.33 (dd, J=14.2, 2.6 Hz, 1H), 3.71–3.78 (m, 2H), 3.93–4.01 (m, 4H), 5.11–5.15 (m, 1H);
ESMS m/e 539 ($M^+$-1); $[\alpha]_D$+15.29 degrees (c 0.0104 g/mL, $CHCl_3$).

Elemental Analysis for $C_{25}H_{49}O_8PS \cdot 0.25 CHCl_3$:

| Calculated: | C, 53.16; H, 8.70; |
|---|---|
| Found: | C, 53.01; H, 8.63. |

EXAMPLE 2

Preparation of (1-Hexanoylthio-1-deoxy-2-hexanoyl-sn-glycero-3-phosphoryl) ethylene glycol

A. 1-Hexanoylthio-1-deoxy-2-hexanoyl-3-(triphenylmethyl)-sn-glycerol

Following the procedure as described in Part D of Example 1, title compound was obtained from 1-thio-1-deoxy-3-(triphenylmethyl)-sn-glycerol in a 76% yield.

IR (CHCl$_3$) 1733, 1690 cm$^{-1}$;

$^1$H NMR (CDCl$_3$) δ0.85–0.95 (m, 6H), 1.25–1.37 (m, 8H), 1.55–1.70 (m, 4H), 2.32 (t, J=7.6 Hz, 2H), 2.48 (t, J=7.5 Hz, 2H), 3.11 (dd, J=14.1, 7.3 Hz, 1H), 3.19–3.21 (m, 2H), 3.28 (dd, J=14.1, 4.8 Hz, 1H), 5.10–5.16 (m, 1H), 7.22–7.32 (m, 9H), 7.40–7.45 (m, 6H);

FDMS m/e 547 (M$^+$+1); [α]$_D$+19.24 degrees (c 0.0092 g/mL, CHCl$_3$).

Elemental Analysis for C$_{34}$H$_{42}$O$_4$S:

| | |
|---|---|
| Calculated: | C, 74.69; H, 7.74; |
| Found: | C, 74.43; H, 8.01. |

B. 1-Hexanoylthio-1-deoxy-2-hexanoyl-sn-glycerol

Following the procedure as described in Part E of Example 1, title compound was obtained from 1-hexanoylthio-1-deoxy-2-hexanoyl-3-(triphenylmethyl)-sn-glycerol in an 85% yield.

IR (CHCl$_3$) 3500, 1731, 1687 cm$^{-1}$;

$^1$H NMR (CDCl$_3$) δ0.89 (t, J=7.0 Hz, 6H), 1.21–1.38 (m, 8H), 1.60–1.72 (m, 4H), 2.30 (br s, 1H), 2.32 (t, J=7.3 Hz, 2H), 2.58 (t, J=7.3 Hz, 2H), 3.10 (dd, J=14.4, 5.4 Hz, 1H), 3.27 (dd, J=14.4, 6.3 Hz, 1H), 3.60–3.70 (m, 2H), 4.92–4.99 (m, 1H);

ESMS m/e 305 (M$^+$+1). [α]$_D$+0.98 degrees (c 0.0590 g/mL, CHCl$_3$).

Elemental Analysis for C$_{15}$H$_{28}$O$_4$S:

| | |
|---|---|
| Calculated: | C, 59.18; H, 9.27; |
| Found: | C, 58.85; H, 9.10. |

C. (1-Hexanoylthio-1-deoxy-2-hexanoyl-sn-glycero-3-phosphoryl)oxy]ethylene glycol Following the procedure as described in Part F of Example 1, title compound was obtained from 1-hexanoylthio-1-deoxy-2-hexanoyl-sn-glycerol.

IR (CHCl$_3$) 3320, 1733, 1691 cm$^{-1}$;

$^1$H NMR (CDCl$_3$) δ0.85–0.95 (m, 6H), 1.22–1.35 (m, 8H), 1.55–1.68 (m, 4H), 2.28 (t, J=7.5 HZ, 2H), 2.53 (t, J=7.5 Hz, 2H), 2.90 (br S, 1H), 3.07 (dd, J=14.2, 6.8 Hz, 1H), 3.31 (dd, J=14.2, 3.9 Hz, 1H), 3.75–3.79 (m, 2H), 3.95–4.10 (m, 4H), 5.10–5.15 (m, 1H);

ESMS m/e 429 (M$^+$+1); [α]$_D$+16.47 degrees (c 0.00085 g/mL, CHCl$_3$).

Elemental Analysis for C$_{17}$H$_{33}$O$_8$PS.0.2CHCl$_3$: Calculated: C, 45.67; H, 7.40; Found: C, 45.45; H, 7.08.

EXAMPLE 3

Preparation of (1-Heptanoylthio-1-deoxy-2-heptanoyl-sn-glycero-3-phosphoryl) ethylene glycol

A. 1-Heptanoylthio-1-deoxy-2-heptanoyl-3-(triphenylmethyl)-sn-glycerol

Following the procedure as described in Part D of Example 1, title compound was obtained from the compound of Example 1, Part C, in a 65% yield.

IR (CHCl$_3$) 1733, 1690 cm$^{-1}$;

$^1$H NMR (CDCl$_3$) δ0.85–0.93 (m, 6H), 1.22–1.38 (m, 12H), 1.55–1.70 (m, 4H), 2.30–2.35 (m, 2H), 2.45–2.52 (m, 2H), 3.08–3.14 (m, 1H), 3.18–3.21 (m, 2H), 3.26–3.32 (m, 1H), 5.11–5.15 (m, 1H), 7.21–7.32 (m, 9H), 7.40–7.45 (m, 6H);

FDMS m/e 574 (M$^+$); [α]$_D$+19.60 degrees (c 0.0100 g/mL, CHCl$_3$).

Elemental Analysis for C$_{36}$H$_{46}$O$_4$S: Calculated: C, 75.22; H, 8.07; Found: C, 75.06; H, 8.07.

B. 1-Heptanoylthio-1-deoxy-2-heptanoyl-sn-glycerol

Following the procedure as described in Part E of Example 1, title compound was obtained from compound 1-heptanoylthio-1-deoxy-2-heptanoyl-3-(triphenylmethyl)-sn-glycerol in a 43% yield.

IR (CHCl$_3$) 3428 (br), 1740, 1696 cm$^{-1}$;

$^1$H NMR (CDCl$_3$) δ0.88 (t, J=6.4 Hz, 6H), 1.22–1.35 (m, 12H), 1.58–1.70 (m, 4H), 2.32 (t, J=7.5 Hz, 2H), 2.38 (br s, 1H), 2.58 (t, J=7.5 Hz, 2H), 3.10 (dd, J=14.3, 5.5 Hz, 1H), 3.27 (dd, J=14.3, 6.2 Hz, 1H), 3.62–3.70 (m, 2H), 4.92–4.98 (m, 1H);

ESMS m/e 333 (M$^+$+1).

C. (1-Heptanoylthio-1-deoxy-2-heptanoyl-sn-glycero-3-phosphoryl) ethylene glycol Following the procedure as described in Part F of Example 1, title compound was obtained from 1-heptanoylthio-1-deoxy-2-heptanoyl-sn-glycerol in a 48% yield.

IR (CHCl$_3$) 3300 (br), 1733, 1691 cm$^{-1}$;

$^1$H NMR (CDCl$_3$) δ0.79–0.83 (m, 6H), 1.10–1.30 (m, 12H), 1,48–1.60 (m, 4H), 2.22 (t, J=7.5 Hz, 2H), 2.46 (t, J=7.5 Hz, 2H), 2.50 (br s, 1H), 3.01 (dd, J=14.2, 8.0 Hz, 1H), 3.26 (dd, J=14.2, 3.7 Hz, 1H), 3.65–3.71 (m, 2H), 3.89–4.00 (m, 4H), 5.02–5.08 (m, 1H);

ESMS mle 455 (M$^+$); [α]$_D$+20.77 degrees (c 0.0065 g/mL, CHCl$_3$)

Elemental Analysis for C$_{19}$H$_{36}$O$_8$PS.0.7H$_2$O:

| | |
|---|---|
| Calculated: | C, 48.75; H, 8.05; |
| Found: | C, 48.76; H, 7.89. |

EXAMPLE 4

Preparation of (1-Octanoylthio-1-deoxy-2-octanoyl-sn-glycero-3-phosphoryl) ethylene glycol

A. 1-Octanoylthio-1-deoxy-2-octanoyl-3-(triphenylmethyl)-sn-glycerol

Following the procedure as described in Part D of Example 1, title compound was obtained from the compound of Example 1, Part C, in an 84% yield.

IR (CHCl$_3$) 1733, 1690 cm$^{-1}$;

$^1$H NMR (CDCl$_3$) δ0.87 (t, J=6.5 Hz, 6H), 1.20–1.35 (m, 16H), 1.56–1.68 (m, 4H), 2.32 (t, J=7.5 Hz, 2H), 2.48 (t, J=7.6 Hz, 2H), 3.11 (dd, J=14.1, 7.6 Hz, 1H), 3.18–3.21 (m, 2H), 3.29 (dd, J=14.1, 4.9 Hz, 1H), 5.11–5.15 (m, 1H), 7.21–7.32 (m, 9H), 7.40–7.45 (m, 6H);

FDMS m/e 603 (M$^+$+1); [α]$_D$+18.56 degrees (c 0.0097 g/mL, CHCl$_3$).

Elemental Analysis for C$_{38}$H$_{50}$O$_4$S:

| | |
|---|---|
| Calculated: | C, 75.71; H, 8.36; |
| Found: | C, 75.63; H, 8.39. |

B. 1-Octanoylthio-1-deoxy-2-octanoyl-sn-glycerol

Following the procedure as described in Part E of Example 1, title compound was obtained from 1-octanoylthio-1-deoxy-2-octanoyl-3-(triphenylmethyl)-sn-glycerol in an 86% yield.

IR (CHCl$_3$) 1731, 1687 cm$^{-1}$;

$^1$H NMR (CDCl$_3$) δ0.88 (t, J=6.9 Hz, 6H), 1.20–1.35 (m, 16H), 1.58–1.70 (m, 4H), 2.20 (br s, 1H), 2.32 (t, J=7.5 Hz, 2H), 2.58 (t, J=7.5 Hz, 2H), 3.10 (dd, J=14.2, 5.3 Hz, 1H), 3.27 (dd, J=14.2, 6.3 Hz, 1H), 3.62–3.71 (m, 2H), 4.92–4.99 (m, 1H);

ESMS m/e 361 (M⁺+1). [α]$_D$+0.27 degrees (c 0.0290 g/mL, CHCl$_3$)

Elemental Analysis for C$_{19}$H$_{36}$O$_4$S:

| Calculated: | C, 63.29; H, 10.06; |
|---|---|
| Found: | C, 63.16; H, 9.97. |

C. (1-Octanoylthio-1-deoxy-2-octanoyl-sn-glycero-3-phosphoryl)oxy]ethylene glycol Following the procedure as described in Part F of Example 1, title compound was obtained from 1-octanoylthio-1-deoxy-2-octanoyl-sn-glycerol in a 56% yield.

IR (CHCl$_3$) 3300, 1735, 1692 cm⁻¹;

¹H NMR (CDCl$_3$) δ0.88 (t, J=6.6 Hz, 6H), 1.20–1.35 (m, 16H), 1,55–1.65 (m, 4H), 2.29 (t, J=7.5 Hz, 2H), 2.53 (t, J=7.8 Hz, 2H), 2.80 (br s, 1H), 3.07 (dd, J=14.2, 7.5 Hz, 1H), 3.31 (dd, J=14.2, 4.4 Hz, 1H), 3.78–3.80 (m, 2H), 3.95–4.10 (m, 4H), 5.08–5.51 (m, 1H);

ESMS m/e 483 (M⁺−1), 484 (M⁺); [α]$_D$+10.80 degrees (c 0.0025 g/mL, CHCl$_3$).

EXAMPLE 5

Preparation of (1-Myristoylthio-1-deoxy-2-myristoyl-sn-glycero-3-phosphoryl) ethylene glycol A. 1-Myristoylthio-1-deoxy-2-myristoyl-3-(triphenylmethyl)-sn-glycerol Following the procedure as described in Part D of Example 1, title compound was obtained from the compound of Example 1, Part C, in an 84% yield.

IR (CHCl$_3$) 1733, 1687 cm⁻¹;

¹H NMR (CDCl$_3$) δ0.88 (t, J=6.8 Hz, 6H), 1.20–1.38 (m, 40H), 1.56–1.70. (m, 4H), 2.30–2.36 (m, 2H), 2.48 (t, J=7.6 Hz, 2H), 3.10 (dd, J=14.0, 7.6 Hz, 1H), 3.19–3.21 (m, 2H), 3.22–3.31 (m, 1H), 5.12–5.18 (m, 1H), 7.20–7.35 (m, 9H), 7.40–7.45 (m, 6H);

FDMS m/e 771 (M⁺); [α]$_D$+15.68 degrees (c 0.0099 g/mL, CHCl$_3$).

Elemental Analysis for C$_{50}$H$_{74}$O$_4$S:

| Calculated: | C, 77.87; H, 9.67; |
|---|---|
| Found: | C, 77.96; H, 9.56. |

B. 1-Myristoylthio-1-deoxy-2-myristoyl-sn-glycerol

Following the procedure as described in Part E of Example 1, title compound was obtained from 1-Myristoylthio-1-deoxy-2-myristoyl-3-(triphenylmethyl)-sn-glycerol in a 90% yield.

IR (CHCl$_3$) 1732, 1687 cm⁻¹;

¹H NMR (CDCl$_3$) δ0.87 (t, J=6.9 Hz, 6H), 1.20–1.34 (m, 40H), 1.58–1.70 (m, 4H), 2.31 (t, J=7.5 Hz, 2H), 2.42 (br s, 1H), 2.57 (t, J=7.6 Hz, 2H), 3.09 (dd, J=14.5, 5.5 Hz, 1H), 3.27 (dd, J=14.5, 6.3 Hz, 1H), 3.62–3.67 (m, 2H), 4.92–4.98 (m, 1H);

ESMS m/e 529 (M⁺+1).

C. (1-Myristoylthio-1-deoxy-2-myristoyl-sn-glycero-3-phosphoryl) ethylene glycol Following the procedure as described in Part F of Example 1, title compound was obtained from 1-myristoylthio-1-deoxy-2-myristoyl-sn-glycerol.

IR (CHCl$_3$) 1735 cm⁻¹;

¹H NMR (CDCl$_3$) δ0.89 (t, J=6.9 Hz, 6H), 1.20–1.37 (m, 40H), 1,55–1.70 (m, 4H), 2.32 (t, J=7.6 Hz, 2H), 2.57 (t, J=7.6 Hz, 2H), 3.09 (dd, J=14.1, 7.0 Hz, 1H), 3.25 (dd, J=14.1, 5.3 Hz, 1H), 3.79–3.84 (m, 2H), 4.10–4.20 (m, 4H), 5.09–5.15 (m, 1H);

ESMS m/e 651 (M⁺−1); [α]$_D$+5.93 degrees (c 0.0045 g/mL, CHCl$_3$).

Elemental Analysis for $C_{33}H_{65}O_8PS \cdot 0.3CHCl_3$:

| Calculated: | C, 58.07; H, 9.55; |
|---|---|
| Found: | C, 58.32; H, 9.33. |

What is claimed is:

1. A compound of formula I (I)

wherein
M is $C_5$–$C_{19}$ alkyl, alkenyl or alkynyl;
Q is nonyl;
Y is $(CH_2)_2OH$ or $CH_2CHOHCH_2OH$.

2. The compound of claim 1 wherein
each of M and Q is nonyl; and
Y is $(CH_2)_2OH$.

3. The compound of claim 1 which is (1-decanoylthio-1-deoxy-2-decanoyl-sn-glycero-3-phosphoryl)ethylene glycol.

4. The compound of claim 1 which is 1-decanoylthio-1-deoxy-2-decanoyl-sn-glycero-3-phosphoryl-1'-sn-glycerol.

5. A compound of formula III

III wherein each of Q and M is independently $C_5$–$C_{19}$ alkyl, alkenyl or alkynyl.

\* \* \* \* \*